(12) United States Patent
Gadsby et al.

(10) Patent No.: US 8,579,886 B2
(45) Date of Patent: Nov. 12, 2013

(54) ACCORDION STYLE CABLE STAND-OFF

(75) Inventors: Peter Gadsby, Broomfield, CO (US);
Dirk I. Johnson, Louisville, CO (US)

(73) Assignee: Covidien LP, Mansfield, MA (US)

( * ) Notice: Subject to any disclaimer, the term of this patent is extended or adjusted under 35 U.S.C. 154(b) by 1712 days.

(21) Appl. No.: 11/799,374

(22) Filed: May 1, 2007

(65) Prior Publication Data
US 2008/0275438 A1 Nov. 6, 2008

(51) Int. Cl.
*A61B 18/14* (2006.01)
(52) U.S. Cl.
USPC .............................. 606/1; 606/34; 248/68.1
(58) Field of Classification Search
USPC ........... 606/32–50, 1; 174/154–166; 242/129, 242/398, 400–407; 604/170–174; 248/68.1
See application file for complete search history.

(56) References Cited

U.S. PATENT DOCUMENTS

| | | | |
|---|---|---|---|
| 641,662 A | 1/1900 | Williams | |
| 700,107 A | 5/1902 | West | |
| 716,115 A | 12/1902 | West | |
| 1,982,885 A | 12/1934 | Stupakoff | |
| 2,118,907 A | 5/1938 | Unterbusch et al. | |
| 2,167,510 A | 7/1939 | Hobart | |
| 3,210,816 A * | 10/1965 | Bette | 128/852 |
| 3,271,506 A | 9/1966 | Martin et al. | |
| 3,286,015 A | 11/1966 | Hildebrand et al. | |
| 3,306,793 A | 2/1967 | Gill et al. | |
| 3,368,564 A * | 2/1968 | Selix | 604/180 |
| 3,586,758 A | 6/1971 | Harmon et al. | |
| 3,716,733 A | 2/1973 | Keith et al. | |
| 4,579,310 A * | 4/1986 | Wells et al. | 248/544 |
| 5,335,663 A | 8/1994 | Oakley et al. | |
| 5,469,853 A | 11/1995 | Law et al. | |
| 5,594,827 A | 1/1997 | Joulie et al. | |
| 5,742,002 A | 4/1998 | Arredondo et al. | |
| 5,906,283 A * | 5/1999 | Kump et al. | 211/54.1 |
| 5,920,032 A | 7/1999 | Aeschbacher et al. | |
| 6,024,740 A | 2/2000 | Lesh et al. | |
| 6,102,192 A * | 8/2000 | Tomuro et al. | 198/747 |
| 6,117,101 A | 9/2000 | Diederich et al. | |
| 6,161,049 A | 12/2000 | Rudie et al. | |
| 6,165,172 A | 12/2000 | Farley et al. | |
| 6,179,832 B1 | 1/2001 | Jones et al. | |
| 6,200,312 B1 | 3/2001 | Zikorus et al. | |
| 6,222,193 B1 | 4/2001 | Thurston et al. | |
| 6,237,606 B1 | 5/2001 | Zikorus et al. | |
| 6,277,083 B1 | 8/2001 | Eggers et al. | |
| 6,471,659 B2 | 10/2002 | Eggers et al. | |
| 6,491,662 B1 | 12/2002 | Liprie et al. | |
| 6,496,737 B2 | 12/2002 | Rudie et al. | |
| 6,514,249 B1 | 2/2003 | Maguire et al. | |
| 6,547,788 B1 | 4/2003 | Maguire et al. | |
| 6,652,515 B1 | 11/2003 | Maguire et al. | |
| 6,682,526 B1 | 1/2004 | Jones et al. | |
| 6,689,126 B1 | 2/2004 | Farley et al. | |
| 6,733,521 B2 | 5/2004 | Chobotov et al. | |

(Continued)

*Primary Examiner* — Michael Peffley

(57) ABSTRACT

A cable stand-off for use with an electrosurgical system includes an accordion body portion having a plurality of panels, and a plurality of hinges. Each panel has at least one hole formed therethrough. The holes of the plurality of panels are axially aligned with one another. The plurality of hinges couples adjacent panels to one another. In one embodiment, the hinges couple adjacent panels in a tip-to-tail fashion. The accordion body portion may be made of a flexible material. Each panels may further include at least one slot extending from a hole to an edge of the panel.

22 Claims, 5 Drawing Sheets

(56) References Cited

U.S. PATENT DOCUMENTS

| | | |
|---|---|---|
| 6,743,983 B2 | 6/2004 | Wiekhorst et al. |
| 6,761,733 B2 | 7/2004 | Chobotov et al. |
| 6,769,433 B2 | 8/2004 | Zikorus et al. |
| 6,923,809 B2 | 8/2005 | Eggers et al. |
| 6,932,776 B2 | 8/2005 | Carr |
| 6,955,653 B2 | 10/2005 | Eggers |
| 7,041,101 B2 | 5/2006 | Eggers |
| 7,049,519 B2 | 5/2006 | Wiekhorst et al. |
| D568,723 S * | 5/2008 | Morgan .......................... D8/356 |
| 7,446,260 B2 * | 11/2008 | Hammonds ................... 174/154 |
| 7,488,199 B2 * | 2/2009 | Gonzalez ...................... 439/502 |
| 7,607,618 B2 * | 10/2009 | Mori et al. ................... 248/68.1 |
| 2001/0016761 A1 | 8/2001 | Rudie et al. |
| 2002/0022833 A1 | 2/2002 | Maguire et al. |
| 2002/0087156 A1 | 7/2002 | Maguire et al. |
| 2002/0103420 A1 | 8/2002 | Coleman et al. |
| 2002/0151953 A1 | 10/2002 | Chobotov et al. |
| 2002/0151956 A1 | 10/2002 | Chobotov et al. |
| 2002/0165535 A1 | 11/2002 | Lesh et al. |
| 2003/0060820 A1 | 3/2003 | Maguire et al. |
| 2004/0024396 A1 | 2/2004 | Eggers |
| 2004/0162555 A1 | 8/2004 | Farley et al. |
| 2004/0243004 A1 | 12/2004 | Carr |
| 2004/0254621 A1 | 12/2004 | Jones et al. |
| 2004/0267258 A1 | 12/2004 | Zikorus et al. |
| 2005/0033286 A1 | 2/2005 | Eggers et al. |
| 2005/0165391 A1 | 7/2005 | Maguire et al. |
| 2005/0167146 A1 | 8/2005 | Wiekhorst et al. |
| 2005/0197570 A1 | 9/2005 | Carr |
| 2005/0203388 A1 | 9/2005 | Carr |
| 2006/0009833 A1 | 1/2006 | Chobotov et al. |
| 2006/0095027 A1 | 5/2006 | Eggers |
| 2013/0138044 A1 * | 5/2013 | Schuman et al. ............. 604/174 |

* cited by examiner

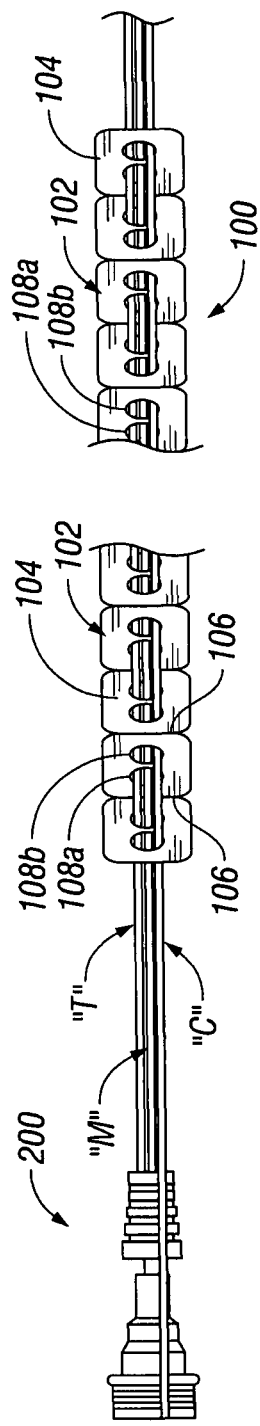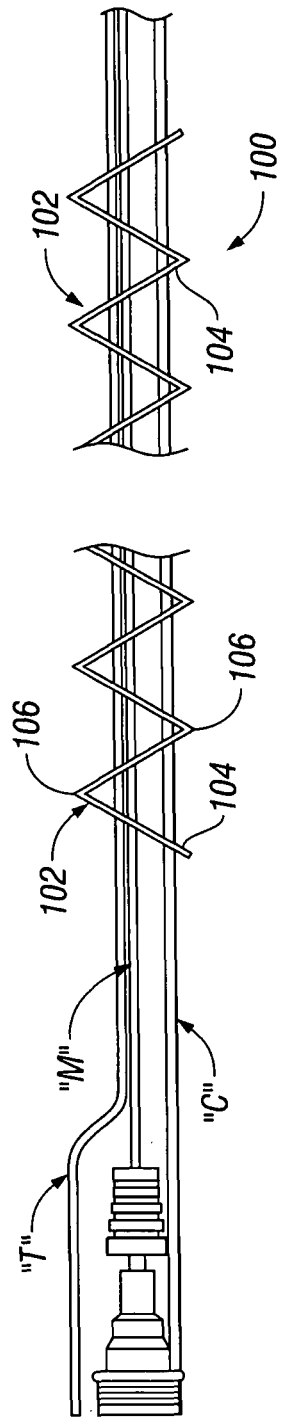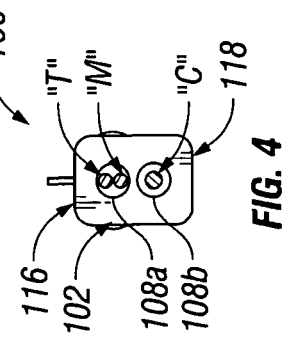

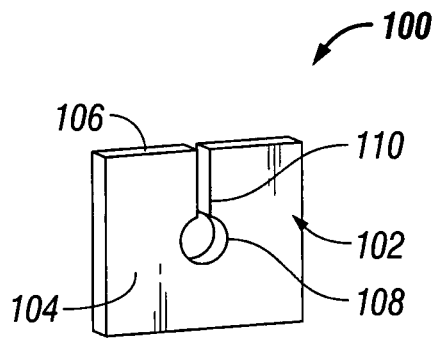
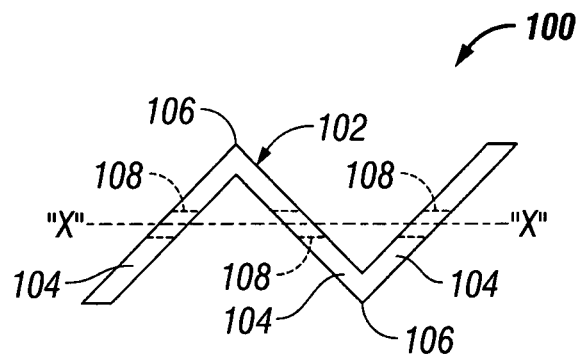
*FIG. 8*  *FIG. 9*
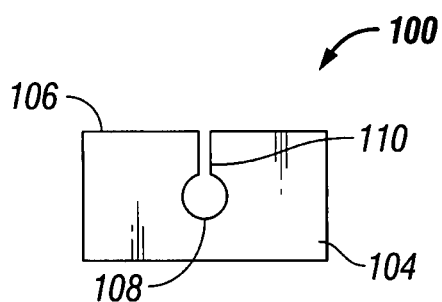
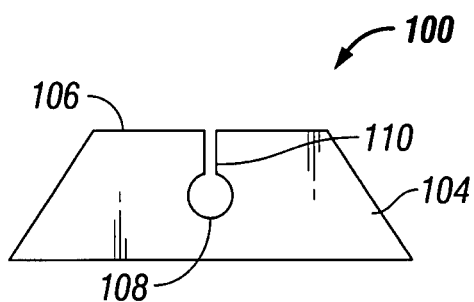
*FIG. 10*  *FIG. 11*
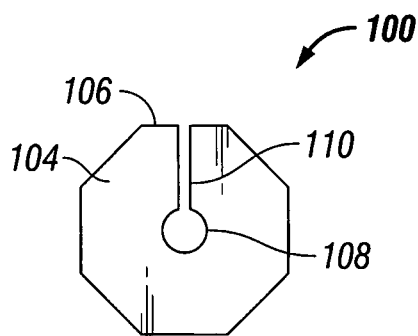
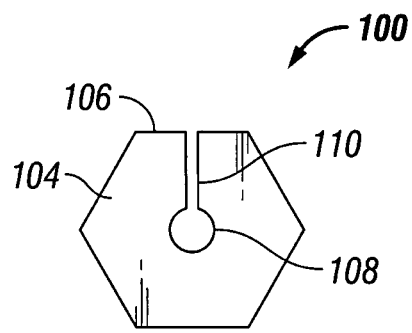
*FIG. 12*  *FIG. 13*

ACCORDION STYLE CABLE STAND-OFF

BACKGROUND

1. Technical Field

The present disclosure relates to a device and method for managing multiple cables, tubing or wires of surgical instruments and devices. More particularly, the present disclosure relates to an accordion style cable stand-off configured to isolate relatively hot cables of surgical systems from surrounding structures.

2. Background of Related Art

Electrosurgical systems are well known in the art. Some electrosurgical systems employ microwave energy to produce a number of therapeutic effects in and/or on tissue at a target surgical site during any number of non-specific surgical procedures. Many electrosurgical systems transmit microwave energy as well as other kinds of energy through conduits, such as, wires, cables, tubing or other suitable energy transmission structure. Generally, the energy transmitted in electrosurgical systems heats the conduits and produces detrimental heat build-up therein and heat transfer to adjacent structure. Accordingly, in operation, it is beneficial to isolate or separate the heated conduit from other structures or objects in order to prevent undesirable heat transfer therebetween.

Usually, electrosurgical systems have multiple energy transmission conduits. Users may often find that managing multiple energy transmission conduits can be a cumbersome process.

SUMMARY

The present disclosure illustrates and describes various embodiments of a cable stand-off for use with an electrosurgical system. The presently disclosed cable stand-off includes an accordion body portion and a plurality of panels having at least one hole formed therethrough. The holes of the plurality of panels are axially aligned with one another. The cable stand-off also has a plurality of hinges coupling adjacent panels to one another. In one embodiment, the hinges couple adjacent panels in a tip-to-tail fashion. The accordion body portion can be made of a flexible material.

The panels of the cable stand-off can have any suitable shape. For instance, the panels may have at least one of a square shape, rectangular shape, trapezoidal shape, hexagonal shape and octagonal shape. Each panel has at least one slot extending from a hole to an edge of the panel. In one embodiment, each panel has a single hole and a corresponding slot. Alternatively, each panel may have two holes and two corresponding slots. The slots of the panels can extend from a respective hole to a common edge of the panel or from a respective hole to an opposed edge of the panel.

During assembly, users may insert a first cable into the holes of the stand-off such that the accordion body portion extends over at least a portion of the length of the first cable. Operations may introduce a second cable into the holes of the cable-stand off. First and second cables can be introduced into the holes or threaded into the holes. The cable stand-off can be collapsed before inserting the first or second cable into the holes. Thereafter, users may expand the cable stand-off. Once a user assembles the cable stand-off, the first or second cable, or both, will be separated from other cables of the electrosurgical system and from the patient.

DESCRIPTION OF THE DRAWINGS

An embodiment of the presently disclosed electrosurgical system and accordion style cable stand-off for use therewith is disclosed herein with reference to the drawings, wherein:

FIG. 2 is a top plan view of the electrosurgical system and the accordion style cable stand-off of FIGS. 1 and 2;

FIG. 3 is a side plan view of the electrosurgical system and the accordion style cable stand-off of FIG. 1;

FIG. 4 is a front elevational view of the electrosurgical system and the accordion style cable of FIGS. 1-3;

FIG. 8 is a front elevational view of a panel of an accordion style cable stand-off according to another embodiment of the present disclosure;

FIG. 9 is a side elevational view of a portion of the accordion style cable stand-off including the panel of FIG. 8;

FIG. 10 is a front elevational view of a panel of an accordion style cable stand-off according to another embodiment of the present disclosure;

FIG. 11 is a front elevational view of a panel of an accordion style cable stand-off according to another embodiment of the present disclosure;

FIG. 12 is a front elevational view of a panel of an accordion style cable stand-off according to another embodiment of the present disclosure;

FIG. 13 is a front elevational view of a panel of an accordion style cable stand-off according to another embodiment of the present disclosure;

DETAILED DESCRIPTION OF EMBODIMENTS

Figure 1:
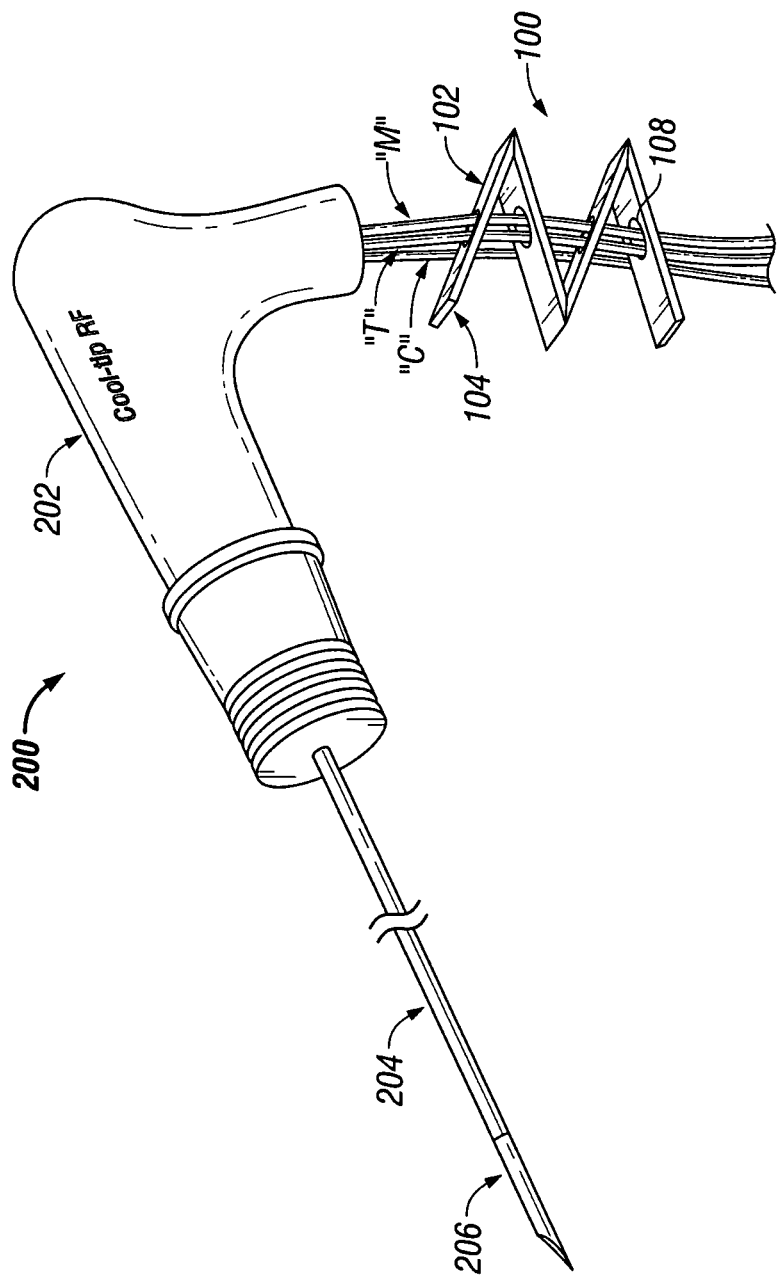
FIG. 1 is a perspective view of an electrosurgical system and an accordion style cable stand-off according to an embodiment of the present disclosure.

Embodiments of the presently disclosed electrosurgical system and accordion style cable stand-off for use therewith are now described in detail with reference to the drawings, in which like reference numerals designate identical or corresponding elements in each of the several views. Terms such as "above", "below", "upper", "lower", "forward", "rearward", etc. refer to the orientation of the figures or the direction of components and are simply used for convenience of description.

Referring initially to FIGS. 1-4, an electrosurgical system, such as a microwave ablation device, is generally designated as reference numeral 200. Electrosurgical system 200 includes a handle portion 202, at least one microwave cable "M", extending from handle portion 202 for connection to an electrosurgical energy source (not explicitly shown), and a tubular member or probe 204 extending from housing portion 202 and terminating in a tip 206. Electrosurgical system 200 may include a fluid conduit "C" extending from a source of cooling fluid (not shown) and ending in tip 206. In operation, cable "M" transmits suitable therapeutic energy from the electrosurgical energy source to tip 206.

With continued reference to FIGS. 1-4, an accordion style cable stand-off, in accordance with an embodiment of the present disclosure, is generally designated as reference numeral 100. As seen in FIGS. 1-4, cable stand-off 100 includes a corrugated or accordion body portion 102 made-up of a plurality of panels 104 joined to one another in end-to-end fashion. Cable stand-off 100 may be formed of paper, plastic, cloth or any other flexible and non-conductive material as deemed suitable by one having ordinary skill in the art.

As seen in FIG. 1, cable stand-off 100 is adapted to be used in combination with electrosurgical system 200. In use, cable stand-off 100 functions to allow convective cooling of conduits, cables, wires, or tubing disposed therethrough and is capable of managing multiple conduits, cables, wires, or tubing during surgical procedures. In one embodiment, cable stand-off 100 functions to maintain a designated conduit spaced a distance from adjacent conduits.

In the embodiment illustrated in FIGS. 1-4, each panel 104 is coupled to an adjacent panel 104 through a living hinge 106. The plurality of panels 104 may have any suitable shape, such as, for example, a square, rectangle, hexagon, or octagon. Each panel 104 includes at least one hole 108 formed therein, as shown in FIG. 1. Alternatively, each panel 104 can include two holes 108a, 108b formed therein, as depicted in FIGS. 2-4. Irrespective of the number of holes 108 on each panel 104, holes 104 can be positioned on any suitable location away from a patient. Each hole 108a, 108b of each panel 104 is longitudinally aligned with a corresponding hole 108a, 108b formed in an adjacent panel 104. Holes 108a, 108b of each panel 104 are arranged so as to be disposed along a longitudinal axis. As seen in FIGS. 1-4, microwave cable "M" and thermocouple "T" may be disposed through hole 108a, and fluid conduit "C" may be disposed through hole 108b. In the depicted embodiments, holes 108a, 108b are circular in shape, but any suitable shape such as an oval, square, hexagon, square, or rectangle, may be utilized.

In use, microwave cable "M" and optionally thermocouple "T" are disposed through holes 108a of each panel 104 of cable stand-off 100 while conduit(s) "C" are disposed through holes 108b of each panel 104 of cable stand-off 100. Other cables, wires or tubing may be disposed through holes 108a, 108b. As will be discussed in further embodiments, panels 104 of the accordion body portion 102 may have more than one slit formed therein for easy insertion of the conduits, cables, wires or tubing into the holes 108.

Figure 5:
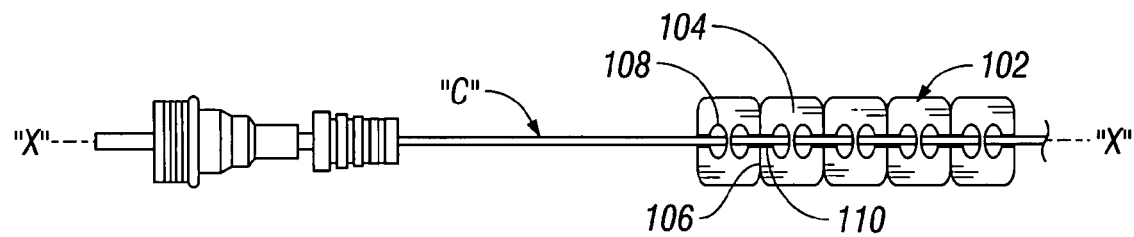
FIG. 5 is a top plan view of a portion of the electrosurgical system and an accordion style cable stand-off according to another embodiment of the present disclosure.
Figure 6:
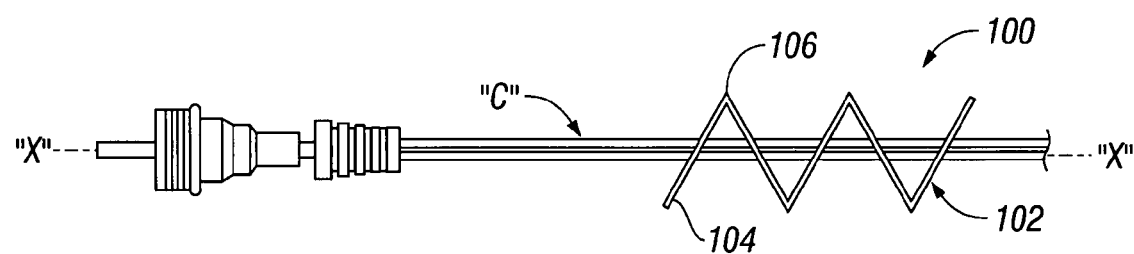
FIG. 6 is a side elevational view of the portion of the electrosurgical system and the accordion style cable stand-off of FIG. 5.
Figure 7:
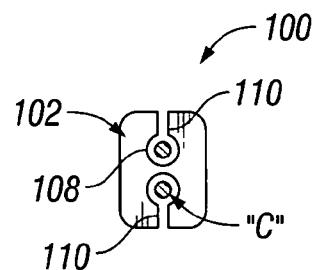
FIG. 7 is a front elevational view of the portion of the electrosurgical system and the accordion style cable stand-off of FIGS. 5 and 6.

With reference to FIGS. 5-9, cable stand-off 100 may include panels 104 having a substantially square shape. Each panel 104 may include a single hole 108, as shown on FIGS. 8-9, or two holes 108, as illustrated in FIGS. 5-7. Panels 104 also have a slot 110 formed therein. Slot 110 extends from a hole 108 to an edge of panel 104. In one embodiment, slots 110 may extend from hole 108 along a central longitudinal axis "X", to living hinge 106. Each hole 108 of each panel 104 is axially aligned along with a corresponding hole 108 formed in an adjacent panel 104. The holes 108 of each panel 104 may be arranged so as to be disposed along central longitudinal axis "X" of the cable stand-off 100.

FIGS. 10-13 illustrate examples of suitable shapes for panels 104 of the cable stand-off 100. For instance, FIG. 10 depicts an alternative embodiment of the cable stand-off 100 in which panels are substantially rectangular in shape. In another embodiment, panels 104 of cable stand-off 100 may be formed as trapezoidal in shape, as shown in FIG. 8. In yet another embodiment, cable stand-off 100 includes a plurality of panels 104 having a substantially octagonal shape, as depicted in FIG. 9. As seen in FIG. 10, panels 104 of cable stand-off 100 may have a substantially hexagonal shape. Notably, the plurality of panels 104 may be formed of any suitable shape.

Referring further to FIGS. 10-13, slots 110 may extend axially from holes 108 in a direction toward an end portion of each panel 104, or toward one of hinges 106. Specifically, each panel 104 includes a slot 110 that extends axially from hole 108 to an upper hinge of panel 104 (as illustrated in FIGS. 10-13).

Figure 14:
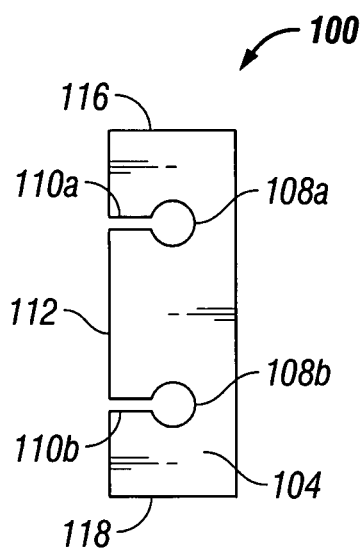
FIG. 14 is a front elevational view of a panel of an accordion style cable stand-off according to another embodiment of the present disclosure.
Figure 15:
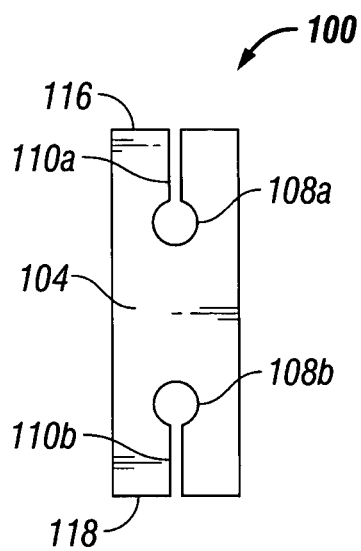
FIG. 15 is a front elevational view of a panel of an accordion style cable stand-off according to another embodiment of the present disclosure.
Figure 16:
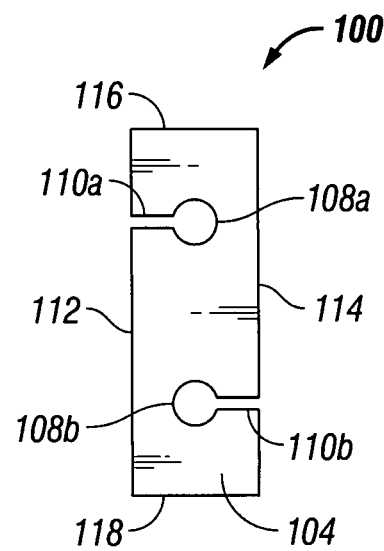
FIG. 16 is a front elevational view of a panel of an accordion style cable stand-off according to another embodiment of the present disclosure.

Turning now to FIGS. 14-16, cable stand-off 100 including panels 104 having a pair of slots 110a, 110b oriented in different directions is shown. As seen in FIG. 14, panel 104 includes a pair of holes, namely an upper and lower hole 108a, 108b formed therein. In the depicted embodiment, panel 104 includes slots 110a, 110b that extend from respective holes 108a, 108b to a common lateral edge 112 of panel 104. In an alternative embodiment, as seen in FIG. 15, slots 110a, 110b spread from respective holes 108a, 108b, in opposite directions, to upper and lower edges 116, 118, respectively, of panel 104. In an alternative embodiment, as seen in FIG. 16, slots 110a, 110b spread from respective holes 108a, 108b, in opposite directions, to respective side edges 112, 114 of panel 104.

Figure 17:
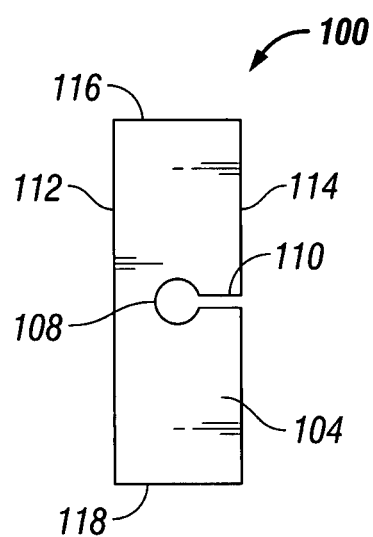
FIG. 17 is a front elevational view of a panel of an accordion style cable stand-off according to another embodiment of the present disclosure.
Figure 18:
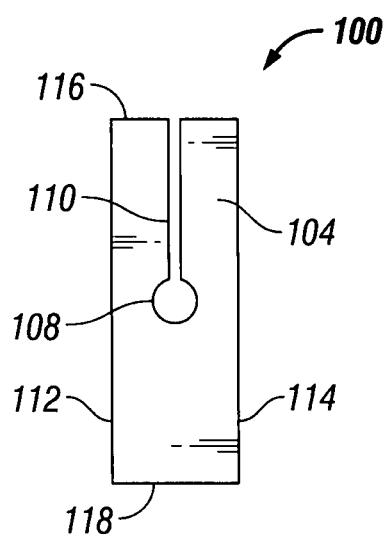
FIG. 18 is a front elevational view of a panel of an accordion style cable stand-off according to another embodiment of the present disclosure.

As seen in FIGS. 17-18, each panel 104 includes a single hole 108 formed therein and a single slot 110 extending from hole 108. Slot 110, as illustrated in FIG. 17, is oriented to extend between hole 108 and lateral edge 114 of panel 104. Alternatively, as seen in FIG. 18, slot 110 is oriented to extend between hole 108 and an upper or lower edge 116, 118 of panel 104.

It is contemplated that one of skill in the art will understand that any of the panels 104 described herein may be combined with any of the different orientations and configurations of slots 110 and holes 108 depicted herein.

According to one method of using cable stand-off 100, cable stand-off 100 is first integrated or assembled to an electrosurgical system 10. During assembly, accordion body 102 may be collapsed and then microwave cable "M" is introduced or threaded through holes 108 or introduced into holes 108 through slots 110. After microwave cable "M" is disposed in holes 108, cable stand-off 100 is expanded or extended along at least a portion of the length of microwave cable "M". Once assembled, cable stand-off 100 maintains microwave cable "M" separated from any other conduit of electrosurgical system 200 and from the patient, thereby reducing heat transfer therebetween.

Accordion style cable stand-off 100 may also me integrated or assembled on to an electrosurgical system with multiple conduits, such as the electrosurgical system 200 depicted in FIGS. 1-4. In use, microwave cable "M" and thermocouple "T" may be placed in and through holes 108a while fluid conduit "C" may be placed in and through holes 108b of cable stand-off 100. In this manner, microwave cable "M" and fluid conduit "F" are separated from one another. This configuration will effectively reduce heat transfer from and between microwave cable "M" to/and fluid conduit "C". In addition, the integration of cable stand-off 100 with electrosurgical system 200 will effectively aid users to manage multiple conduits in electrosurgical system 10.

As hereinabove discussed, cable stand-off 100 may be made of any suitable flexible and non-conductive material known in the art. For instance, plastic, paper, cardboard, and rubber may be used to form cable stand-off 100.

The applications of the accordion style cable stand-offs and methods of using the assemblies discussed above are not limited to electrosurgical systems used for microwave ablation, hyperthermic, and coagulation treatments but may include any number of further electrosurgical applications. Modifications of the above-described assemblies and methods for using the same, and variations of aspects of the disclosure that are obvious to those of skill in the art are intended to be within the scope of the claims.

What is claimed is:

1. A cable stand-off, comprising:
   an accordion body portion including:
      a plurality of panels each having at least two holes formed therethrough, wherein the holes of the plurality of panels are axially aligned with one another, each panel defining a plane;
      a plurality of hinges coupling adjacent panels to one another, each hinge defining a hinge axis of rotation; and
      wherein the at least two holes of each panel are aligned along a central axis of the panel that is oriented orthogonal to the hinge axis of rotation of one of the plurality of hinges.

2. The cable stand-off according to claim 1, wherein the hinges couple adjacent panels in a tip-to-tail fashion.

3. The cable stand-off according to claim 1, wherein the accordion body portion is made of a flexible material.

4. The cable stand-off according to claim 1, wherein the each panel has at least one of a square shape, rectangular shape, trapezoidal shape, hexagonal shape and octagonal shape.

5. The cable stand-off according to claim 1, further comprising at least one slot in each panel extending from at least one of the at least two holes to a side edge of the panel.

6. The cable stand-off according to claim 1, wherein each hole of each panel has a slot extending therefrom.

7. The cable stand-off according to claim 6, wherein each slot extends from a respective hole to a common side edge of the panel.

8. The cable stand-off according to claim 6, wherein a first one of the slots extends from a first one of the at least two holes to a side edge of the panel and a second one of slots extends from a second one of the at least two holes to an opposite side edge of the panel.

9. The cable stand-off according to claim 1, wherein the hinge axes of rotation of the plurality of hinges are substantially parallel to one another.

10. In an improved electrosurgical system having a handle portion, an energy delivery probe extending from the handle, an energy transmitting cable extending from the handle and connected to the probe, wherein the improvement comprises:
    a cable stand-off including:
       an accordion body portion including:
          a plurality of panels each having at least two holes formed therethrough, wherein the holes of the plurality of panels are axially aligned with one another, each panel defining a plane;
          a plurality of hinges coupling adjacent panels to one another, each hinge defining a hinge axis of rotation; and
          wherein the at least two holes of each panel are aligned along a central axis of the panel that is oriented orthogonal to the hinge axis of rotation of one of the plurality of hinges.

11. The electrosurgical system according to claim 10, wherein the hinges couple adjacent panels in a tip-to-tail fashion.

12. The electrosurgical system according to claim 10, wherein the accordion body portion is made of a flexible material.

13. The electrosurgical system according to claim 10, wherein the each panel has at least one of a square shape, rectangular shape, trapezoidal shape, hexagonal shape and octagonal shape.

14. The electrosurgical system according to claim 10, further comprising at least one slot in each panel extending from at least one of the at least two holes to a side edge of the panel.

15. The electrosurgical system according to claim 10, wherein each hole of each panel has a slot extending therefrom.

16. The electrosurgical system according to claim 15, wherein each slot extends from a respective hole to a common side edge of the panel.

17. The electrosurgical system according to claim 15, wherein a first one of the slots extends from a first one of the at least two holes to a side edge of the panel and a second one of slots extends from a second one of the at least two holes to an opposite side edge of the panel.

18. The cable stand-off according to claim 10, wherein the hinge axes of rotation of the plurality of hinges are substantially parallel to one another.

19. The method of managing cables of an electrosurgical system, comprising the steps of:
    providing a cable stand-off including:
       an accordion body portion having:
          a plurality of panels each having at least two holes formed therethrough, wherein the holes of the plurality of panels are axially aligned with one another, each panel defining a plane;
          a plurality of hinges coupling adjacent panels to one another, each hinge defining a hinge axis of rotation; and
          wherein the at least two holes of each panel are aligned along a central axis of the panel that is oriented orthogonal to the hinge axis of rotation of one of the plurality of hinges; and
    inserting a first cable of the electrosurgical system into the holes of the stand-off such that the accordion body portion extends over at least a portion of the length of the first cable.

20. The method of managing cables of an electrosurgical system according to claim 19, further comprising the step of inserting a second cable of the electrosurgical system into the holes of the cable stand-off such that the accordion body portion extends over at least a portion of the length of the second cable.

21. The method of managing cables of an electrosurgical system according to claim 19, further comprising the steps of collapsing the cable stand-off prior to inserting the first cable and expanding the cable stand-off after inserting the first cable.

22. The method of managing cables of an electrosurgical system according to claim 19, wherein the step of inserting the first cable of the electrosurgical system into the holes of cable stand-off, includes:
    introducing the first cable of the electrosurgical system in the holes of the cable stand-off through slots.

* * * * *